United States Patent [19]

Müller et al.

[11] 4,143,220
[45] Mar. 6, 1979

[54] POLYURETHANES PREPARED WITH NOVEL MANNICH BASES

[75] Inventors: Erwin Müller; Heinz Thomas, both of Leverkusen, Fed. Rep. of Germany

[73] Assignee: Bayer Aktiengesellschaft, Leverkusen, Fed. Rep. of Germany

[21] Appl. No.: 658,644

[22] Filed: Feb. 17, 1976

Related U.S. Application Data

[63] Continuation of Ser. No. 495,136, Aug. 6, 1974, abandoned, which is a continuation-in-part of Ser. No. 357,965, May 7, 1973, abandoned, and a continuation-in-part of Ser. No. 398,264, Sep. 17, 1973, abandoned.

[30] Foreign Application Priority Data

May 13, 1972 [DE] Fed. Rep. of Germany ....... 2223427
Sep. 20, 1972 [DE] Fed. Rep. of Germany ....... 2246108

[51] Int. Cl.² .................... C08G 18/14; C08G 18/18
[52] U.S. Cl. .................. 521/129; 260/551 R; 260/561 R; 260/18 TN; 428/425; 521/51; 521/111; 528/54; 560/159
[58] Field of Search ............ 260/2.5 AM, 2.5 AQ, 260/2.5 AC, 561 R, 77.5 AM, 77.5 AQ, 77.5 AC, 75 NQ, 75 NC, 482 C, 551 R; 521/129; 528/54

[56] References Cited

U.S. PATENT DOCUMENTS

| 3,001,955 | 9/1961 | Taub | 260/2.5 |
|---|---|---|---|
| 3,004,933 | 10/1961 | Müller et al. | 260/2.5 |
| 3,050,475 | 8/1962 | Müller et al. | 260/2.5 |
| 3,073,787 | 1/1963 | Krakler | 260/2.5 |
| 3,243,389 | 3/1966 | Moller et al. | 260/2.5 |
| 3,321,415 | 5/1967 | Hennig et al. | 260/2.5 |
| 3,368,985 | 2/1968 | Wismer et al. | 260/2.5 |
| 3,494,933 | 2/1970 | Farrissey, Jr. et al. | 260/2.5 |
| 3,595,814 | 7/1971 | Lloyd et al. | 260/2.5 |

FOREIGN PATENT DOCUMENTS

1229288 11/1966 Fed. Rep. of Germany .......... 260/77.5
1293950 10/1972 United Kingdom .................... 260/77.5

OTHER PUBLICATIONS

Müller and Thomas, Angewandte Macromolekulare Chemie 34, No. 507 (1973) pp. 111–133.

*Primary Examiner*—H.S. Cockeram
*Attorney, Agent, or Firm*—Gene Harsh; Joseph C. Gil

[57] ABSTRACT

Cellular and non-cellular polyurethane plastics and semi-hard polyurethane foams which are prepared by the use of novel Mannich bases of the general formula

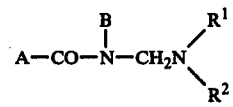

and which have improved strength and tear resistance are disclosed herein.

6 Claims, No Drawings

POLYURETHANES PREPARED WITH NOVEL MANNICH BASES

This is a continuation of application Ser. No. 495,136, filed Aug. 6, 1974, and now abandoned, which is a continuation-in-part of Ser. No. 357,965, filed May 7, 1973, and a continuation-in-part of Ser. No. 398,264, filed Sept. 17, 1973, both now abandoned.

This invention relates to polyurethane foams prepared using novel Mannich bases.

The preparation of Mannich bases by, for example, reacting carboxylic acid amides or urethanes with aldehydes, such as formaldehyde, and secondary amines is well known as described in "Die Makromolekulare Chemie," Vol. 57, page 45 (1962).

Similarly, the production of polyurethanes from polyisocyanates, relatively high molecular weight polyols and low molecular weight alcohols or amines which have a crosslinking or chain extending effect, optionally in the presence of activators, expanding agents or other ancillarily additives, is also well known.

It is therefore, an object of this invention to provide polyurethanes which have been prepared with a heretofore unknown class of Mannich bases. An additional object of this invention is to provide semi-rigid polyurethane foams having improved physical properties. Yet another object of this invention is to provide semi-rigid polyurethane foams having increased tensile strength and tear resistance. Still a further object of this invention is to provide semi-rigid polyurethane foams having high bond strengths with polymer-based plastics, in the absence of other adhesives. A further additional object of this invention is to provide semi-rigid polyurethane foams having high bond strengths with acrylonitrile-butadiene-styrene polymers or polyvinyl chloride polymers in the absence of other adhesives.

The foregoing objects and others which will become apparent from the following description are accomplished in accordance with the invention, generally speaking, by providing Mannich bases of the general formula:

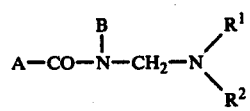

wherein
A is ①- $OR^9$

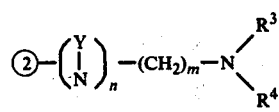

-continued

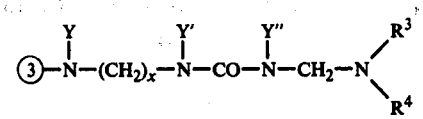

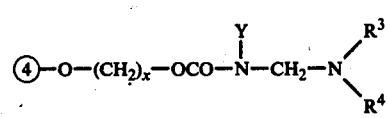

m is an integer of from 1 to 8, preferably 1 or 2;
n is an integer equal to 1 when m is 1 and otherwise is 0;
x is an integer of from 1 to 6;
B is —H
$C_1$-$C_{16}$ alkyl
or when A is ① or when A is ② and n is 0

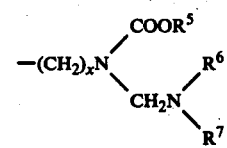

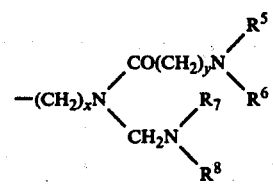

but preferably —H;
y is an integer from 2 to 8 but preferably 2;
$R^1$ through $R^9$ are the same or different and are $C_1$-$C_{12}$ alkyl or —$(CH_2)_y$—OH;
Y, Y', Y'' are the same or different and are H or $C_1$-$C_{16}$ alkyl.

The Mannich bases of the invention are prepared by reacting acid amides with formaldehyde and secondary amines, which acid amides and secondary amines are respectively of the following general formulae:

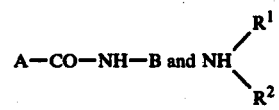

Compounds of the following formulae are representative but by no means exhaustive of the novel Mannich bases of the invention:

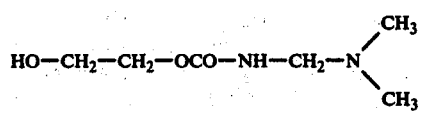

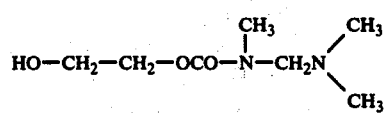

-continued

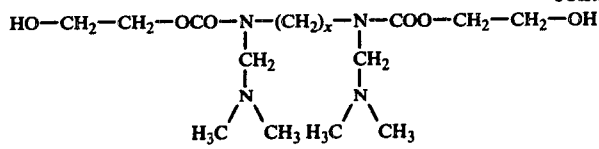

x is an integer of from 1 to 6,

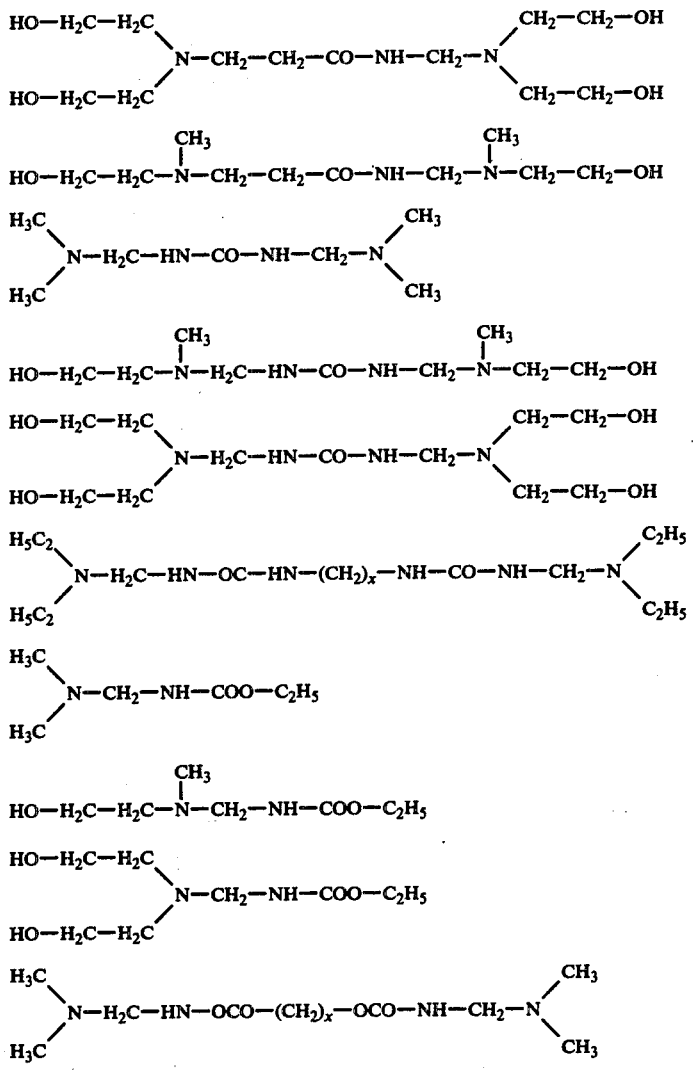

As previously mentioned the Mannich bases of the invention are prepared by conventional methods, well known to the art, by reacting acid amides with formaldehyde and secondary amines. Suitable starting materials are acid amides, such as for example, acrylamide, $\beta$-hydroxyethylurethane, N-methyl-$\beta$-hydroxy ethyl urethane and the like. Of the secondary amines, N-methyldiethanolamine, di-$\beta$-hydroxyethylamine, diethanolamine and dimethylamine may be mentioned. The formaldehyde is ordinarily employed as a 30% aqueous solution. The preparation of the Mannich bases of the invention is fully detailed in the Examples.

The polyisocyanates used as starting components according to the invention may be aliphatic, cycloaliphatic, araliphatic, aromatic or heterocyclic polyisocyanates such as those described e.g. by W. Siefgen in Justus Liebigs Annalen der Chemie, 562, pages 75 to 136, for example, ethylene diisocyanate, tetramethylene-1,4-diisocyanate, hexamethylene-1,6-diisocyanate, dodecane-1,12-diisocyanate, cyclobutane-1,3-diisocyanate, cyclohexane-1,3 and -1,4-diisocyanate and any mixtures of these isomers; 1-isocyanato-3,3,5-trimethyl-5-isocyanatomethyl-cyclohexane (U.S. Pat. No. 3,401,190) hexahydrotolylene-2,4- and -2,6-diisocyanate and any mixtures of these isomers; hexahydrophenylene-1,3- and/or -1,4-diisocyanate, perhydrodiphenylmethane-2,4'- and/or 4,4'-diisocyanate, phenylene-1,3- and -1,4-diisocyanate; tolylene-2,4- and -2,6-diisocyanate and any mixture of these isomers, diphenylmethane-2,4'- and/or 4,4'-diisocyanate, naphthylene-1,5-diisocyanate, triphenylmethane-4,4',4''-triisocyanate, polyphenyl-polymethylene polyisocyanates which can be obtained by anilineformaldehyde condensation followed by phosgenation and have been described e.g. in British Pat. Nos. 874,430 and 848,671, perchlorinated aryl polyisocyanates as described e.g. in German Auslegeschrift No. 1,157,601, polyisocyanates which contain carbodiimide groups as described in German Pat. No. 1,092,007, the diisocyanates described in U.S. Pat. No. 3,492,330, polyisocyanates which contain allophanate groups as described e.g. in British Pat. No. 994,890, Belgian Pat. No. 761,626 and published Dutch Pat. Application No. 7,102,524, polyisocyanates which contain isocyanurate groups as described e.g. in German Patent Nos. 1,022,789, 1,222,067 and 1,027,394 and in German Offenlegungsschriften Nos. 1,929,034 and 2,004,048, polyisocyanates which contain urethane groups as described e.g. in U.S. Pat. Nos. 3,394,164, polyisocyanates which contain acylated urea groups in accordance with U.S. Pat. No. 3,517,039, polyisocyanates which contain biuret groups as described e.g. in German Pat. No. 1,101,394, in British Pat. No. 889,050 and in French Pat. No. 7,017,514, polyisocyanates prepared by telomerization reactions as described, e.g. in Belgian Pat. No. 723,640, polyisocyanates which contain ester groups as described e.g. in British Pat. Nos. 956,474 and 1,072,956, in U.S. Pat. No. 3,567,763 and in German Pat. No. 1,231,688, and reaction products of the above mentioned diisocyanates with acetals in accordance with German Pat. No. 1,072,385.

The isocyanate group-containing distillation residues obtained from the commercial production of isocyanates may also be used, optionally as solutions in one or more of the above mentioned polyisocyanates. Any mixtures of the above mentioned polyisocyanates may also be used.

It is generally preferred to use the commercially readily available polyisocyanates such as tolylene-2,4- and -2,6-diisocyanate and any mixtures of these isomers (TDI), polyphenyl-polymethylene-polyisocyanates which can be obtained by aniline-formaldehyde condensation followed by phosgenation (crude MDI) and polyisocyanates which contain carbodiimide groups, urethane groups, allophanate groups, isocyanurate groups, urea groups or biuret groups (modified polyisocyanates).

Compounds which contain at least two hydrogen atoms that are reactive with isocyanates and which generally have a molecular weight of 400 to 10,000 may also be used as starting components according to the invention. Apart from compounds which contain amino groups, thiol groups or carboxyl groups, these are preferably polyhydroxyl compounds and particularly those which contain 2 to 8 hydroxyl groups, especially those which have a molecular weight of 800 to 10,000 and preferably 1,000 to 6,000 e.g. polyesters, polyethers, polythioethers, polyacetals, polycarbonates or polyester amides which contain at least two, generally 2 to 8, but preferably 2 to 4 hydroxyl groups, such as those known per se for the preparation of homogeneous and cellular polyurethanes.

Suitable polyesters with hydroxyl groups are e.g. reaction products of polyhydric, preferably dihydric alcohols and optionally in addition trihydric alcohols with polybasic, preferably dibasic, carboxylic acids. Instead of free polycarboxylic acids, the corresponding polycarboxylic acid anhydrides or corresponding polycarboxylic acid esters of low alcohols or their mixtures may be used for the preparation of the polyesters. The polycarboxylic acids may be aliphatic, cycloaliphatic, aromatic and/or heterocyclic and may be substituted, e.g. by halogen atoms and/or unsaturated. The following are examples: succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids such as oleic acid, optionally mixed with monomeric fatty acids, dimethyl terephthalate and bis-glycol ester of terephthalic acid. The polyhydric alcohols may be e.g. ethylene glycol, propylene-1,2- and -1,3-glycol, butylene-1,4 and -2,3-glycol, hexane-1,6-diol, octane-1,8-diol, neopentyl glycol, cyclohexane dimethanol (1,4-bis-hydroxymethylcyclohexane), 2-methyl-propane-1,3-diol, glycerol, trimethylolpropane, hexane-1,2,6-triol, butane-1,2,4-triol, trimethylolethane, pentaerythritol, quinitol, mannitol and sorbitol, methyl glycoside, diethylene glycol, triethylene glycol, tetraethylene glycol, polyethylene glycols, dipropylene glycol, polypropylene glycols, dibutylene glycol and polybutylene glycols. The polyesters may contain a proportion of terminal carboxyl groups. Polyesters obtained from lactones, e.g. $\epsilon$-caprolactone or hydroxycarboxylic acids, e.g. $\omega$-hydroxy-caproic acid, may also be used.

The polyethers used according to the invention which contain at least two, generally 2 to 8, and preferably 2 to 3 hydroxyl groups are also known per se and are prepared e.g. by the polymerization of epoxides such as ethylene oxide, propylene oxide, butylene oxide, tetrahydrofuran, styrene oxide or epichlorohydrin either with themselves, e.g. in the presence of $BF_3$, or by addition of these epoxides, optionally as mixtures or successively, to starting components which contain reactive hydrogen atoms such as alcohols or amines, e.g. water, ethylene glycol, propylene-1,3- or -1,2-glycol, trimethylolpropane, 4,4'-dihydroxydiphenylpropane, aniline, ammonia, ethanolamine or ethylene diamine. The sucrose polyethers which have been described in German Auslegeschriften No. 1,176,358 and 1,064,938 may also be used according to the invention. It is frequently preferred to use polyethers which contain predominantly primary OH groups (up to 90% by weight, based on all the OH groups present in the polyether). Polyethers which have been modified with vinyl polymers, e.g. the products obtained by the polymerization of styrene or acrylonitrile in the presence of polyethers (U.S. Pat. Nos. 3,383,351, 3,304,273, 3,523,093 and 3,110,695 and German Patent No. 1,152,536) are suitable as well as polybutadienes which contain OH groups.

Among the polythioethers there should particularly be mentioned the condensation products of thiodiglycol with itself and/or with other glycols, dicarboxylic acids, formaldehyde, aminocarboxylic acids or amino alcohols. Depending on the co-component, these products are polythio mixed ethers, polythio ether esters or polythioether ester amides.

The polyacetals used may be e.g. those compounds which can be prepared from glycols such as diethylene glycol, triethylene glycol, 4,4'-dihydroxyethoxydiphenyldimethyl methane, hexanediol and formaldehyde. Polyacetals suitable for the invention may also be obtained by the polymerization of cyclic acetals.

The hydroxyl polycarbonates used may be known per se, e.g. those which can be prepared by reacting diols such as propane-1,3-diol, butane-1,4-diol and/or hexane-1,6-diol, diethylene glycol, triethylene glycol or tetraethylene glycol with diarylcarbonates such as diphenylcarbonate or phosgene.

The polyester amides and polyamides may be e.g. the predominantly linear condensates obtained from polybasic saturated and unsaturated carboxylic acids or their anhydrides and polyvalent saturated and unsaturated amino alcohols, diamines, polyamines and their mixtures.

Polyhydroxyl compounds which already contain urethane or urea groups as well as natural polyols which may be modified, such as castor oil, carbohydrates or starch may also be used. Addition products of alkylene oxides to phenol formaldehyde resins or to urea formaldehyde resins may be used according to the invention.

Representatives of these compounds which may be used according to the invention have been described e.g. in High Polymers, Vol. XVI, "Polyurethanes: Chemistry and Technology" published by Saunders-Frisch, Interscience Publishers, New York, London, Volume I, 1962, pages 32–42 and pages 44–54 and Volume II, 1964, pages 5–6 and 198–199 and in Kunststoff-Handbuch, Volume VII, Vieweg-Hochtlen, Carl-Hanser Verlag, Munich 1966, e.g. on pages 45 to 71.

Water and/or readily volatile organic substances are frequently used as blowing agents in accordance with the invention. The organic blowing agents may be e.g. acetone, ethyl acetate, halogenated alkanes such as methylene chloride, chloroform, ethylidene chloride, vinylidene chloride, monofluorotrichloromethane, chlorodifluoromethane, or dichlorodifluoromethane, butane, hexane, heptane, or diethylether. A blowing action can also be obtained by the addition of compounds which decompose at temperatures above room temperature to liberate gases, for example, nitrogen e.g. azo compounds such as azoisobutyric acid nitrile. Further examples of blowing agents and details of the use of blowing agents have been described in Kunststoff-Handbuch, Volume VII, published by Vieweg and Hochtlen, Carl-Hanser-Verlag, Munich 1966, e.g. on pages 108–109, 453 to 455 and 507 to 510.

Catalysts are often used in accordance with the invention. The catalysts added are known per se, e.g. tertiary amines such as triethylamine or tributylamine, N-methyl-morpholine, N-ethyl-morpholine, N-cocomorpholine, N,N,N',N'-tetramethyl-ethylene diamine, 1,4-diazabicyclo-(2,2,2)-octane, N-methyl-N'-dimethyl-aminoethyl-piperazine, N,N-dimethylbenzylamine, bis-(N,N-di-ethylaminoethyl)-adipate, N,N-diethylbenzylamine, pentamethyldiethylene triamine, N,N-dimethylcyclohexylamine, N,N,N',N'-tetramethyl-1,3-butanediamine, N,N-dimethyl-β-phenyl-ethylamine, 1,2-dimethyl-imidazole or 2-methylimidazole.

Tertiary amines containing hydrogen atoms which are reactive with isocyanate groups, are e.g. triethanolamine, triisopropanolamine, N-methyl-diethanolamine, N-ethyl-diethanolamine, N,N,-dimethylethanolamine and their reaction products with ethylene oxides such as propylene oxide and/or ethylene oxide.

The catalysts used may also be silaamines which contain carbon-silicon bonds as described, e.g. in German Pat. Specification No. 1,229,290, e.g. 2,2,4-trimethyl-2-silamorpholine or 1,3-diethylaminomethyl-tetramethyl-disiloxane.

The catalysts used may also be bases which contain nitrogen, such as tetraalkylammonium hydroxides, or alkali metal hydroxides such as sodium hydroxide, alkali metal phenolates such as sodium phenolate or alkali metal alcoholates such as sodium methylate. Hexahydrotriazines may also be used as catalysts.

Organic metal compounds may also be used as catalysts according to the invention, especially organic tin compounds.

The organic tin compounds used are preferably tin (II) salts of carboxylic acids such as tin (II) acetate, tin (II) octoate, tin (II) ethylhexoate and tin (II) laurate and the dialkyl tin salts of carboxylic acids such as dibutyl tin diacetate, dibutyl tin dilaurate, dibutyl tin maleate or dioctyl tin diacetate.

Other representatives of the catalysts which may be used in accordance with the invention and details of their action have been described in Kunststoff-Handbuch, Volume VII, published by Vieweg and Hochtlen, Carl-Hanser-Verlag, Munich 1966, e.g. on pages 96 to 102.

The catalysts are generally used in an amount of between about 0.001 and 10% by weight, based on the quantity of compounds with a molecular weight of 400 to 10,000 which contain at least two hydrogen atoms which are reactive with isocyanates.

Surface active additives may also be used in accordance with the invention (emulsifiers and foam stabilizers). The emulsifiers used may be e.g. the sodium salts of castor oil sulphonates or of fatty acids or salts of fatty acids with amines such as oleic acid diethylamine or stearic acid diethanolamine. Alkali metal or ammonium salts of sulphonic acids such as dodecylbenzenesulphonic acid or dinaphthylmethane disulphonic acid or of fatty acids such as ricinoleic acid or of polymeric fatty acids may also be used as surface active additives.

The foam stabilizers used are mainly water-soluble polyether siloxanes. The structure of these compounds is generally such that a copolymer of ethylene oxide and propylene oxide is linked to a polydimethylsiloxane radical. Such foam stabilizers have been described e.g. in U.S. Pat. No. 2,764,565.

Reagents which retard the reaction may also be used in accordance with the invention, e.g. substances which are acid in reaction such as hydrochloric acid or organic acid halides. Cell regulators known per se such as paraffins or fatty alcohols or dimethylpolysiloxanes, pigments or dyes and flame retarding agents known per se, e.g. trischloroethylphosphate or ammonium phosphate and polyphosphate, stabilizers which stabilize against ageing and weathering, plasticizers and fungistatic and bacteriostatic substances and fillers such as barium sulphate, kieselguhr, carbon black or prepared chalk may also be added.

Other examples of surface active additives, foam stabilizers and cell regulators, agents which retard the reaction, stabilizers, flame retarding substances, plasticizers, dyes, fillers and fungistatic and bacteriostatic substances as well as details concerning the use and action of these additives have been described in Kunststoff-Handbuch Volume VI, published by Vieweg and Hochtlen, Carl-Hanser-Verlag, Munich 1966, e.g. on pages 103–113.

According to the invention, the starting components are reacted together by the one-step process, prepolymer process or semi-prepolymer process known per se, frequently with the aid of mechanical devices such as those described in U.S. Pat. No. 2,764,565. Apparatus which would be suitable for carrying out the invention have been described in Kunststoff-Handbuch Volume VI, published by Vieweg and Hochtlen, Carl-Hanser-Verlag, Munich 1966, e.g. on pages 121–205.

The reaction components are reacted at a characteristic of generally between 90 and 110, i.e. the ratio of isocyanate groups to active hydrogen atoms is from about 0.9:1 to about 1.1:1. For example, at a characteristic of 100, the stoichiometric ratio of reactive hydrogen atoms to isocyanate groups is 1:1.

In the production of polyurethanes in accordance with the invention, the Mannich bases according to the invention is used advantageously in a quantity of at least about 3 parts by weight and more preferably in a quantity of from about 3 to about 50 parts by weight, based on 100 parts by weight of the polyhydroxyl compound of molecular weight 800 to 10,000.

For producing semi-rigid foam resins, the reaction mixture is introduced into a mold, frequently one which is lined with a synthetic resin foil which has preferably been vacuum formed. The material used for the mold may be a metal e.g. aluminum, or synthetic resin, e.g. epoxide resin. The reaction mixture foams up in the mold to form the mold product. The foaming process may be carried out in such a way that the molded product has a cellular structure on the surface or it may be carried out to produce a molded product with a compact skin and cellular core. According to the invention, just sufficient reaction mixture may be introduced into the mold so that the resulting foam just fills the mold. Alternatively, a larger amount of reaction mixture than is required for filling the interior of the mold with foam may be introduced. In that case, foaming is said to be carried out under conditions of overcharging, a method of procedure which has already been disclosed, e.g. in U.S. Pat. No. 3,178,490 or U.S. Pat. No. 3,182,104. Semi-rigid foams are preferred according to the invention.

Waxy mold parting agents known per se are frequently used for the process of foaming in the mold.

The semi-rigid foams can be used in particular in the upholstery field. It is possible to produce both thin-layer and also thick-walled foam moldings which, as a rule, can readily be removed from the mold only 10 minutes after the beginning of foaming.

The polyurethanes which can be produced in accordance with the invention can, of course, also be used in other fields, for example as lacquers, coating materials, elastomers or in the production of microporous films, for the production of polyurethane dispersions or in the application of polyurethanes to agriculture, for example, as plant cultivating substrate.

The invention is illustrated but is not intended to be limited by the following Examples, wherein all parts are by weight unless otherwise indicated.

EXAMPLES

EXAMPLE 1

The compound:

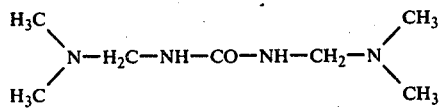

is prepared by introducing 3000 parts of dimethylamine solution (45%, 30 mol) with stirring and water cooling at a reaction temperature of 30° to 45° C. into a suspension of 600 parts of urea (10 mol) in 2000 parts of aqueous formaldehyde solution (30%, 20 mol) which has been adjusted to pH 8 to 9 by the addition of dimethyl amine solution. The reaction mixture is then stirred for 4 hours at 70° C. and the water is evaporated off under vacuum. 1262 parts of a water soluble viscous oil which cannot be distilled are obtained.

Yield: 1262 parts
$C_7H_{18}ON_4$ Molecular weight: 174
Analysis of elements:
Calculated: C 48.5%; H 10.3%; O 9.2%; N 32.1%.
Found: — C 45.3%; H 10.1%; O 12.2%; N 33.4%.

3 parts of this compound is mixed with 90 parts of a polyether with a molecular weight of 4800 which has been obtained by the addition of propylene oxide (87% by weight) and ethylene oxide (13% by weight) to trimethylolpropane, 5 parts of triethanol amine, 2 parts of tall oil and 2.5 parts of water.

This mixture is thoroughly mixed with stirring with 60 parts of a polyphenyl-polymethylene-polyisocyanate which has been obtained by the phosgenation of an aniline-formaldehyde condensate and which has an NCO content of 31%. The foamable reaction mixture is introduced into an aluminum mold which is lined with a vacuum formed ABS/PVC foil (foil of an acrylonitrile-butadiene-styrene copolymer which contains polyvinyl chloride as plasticizer). The foaming reaction sets in immediately after the introduction of the mixture. The degree of compression is about 1:2. A foam which has the following properties is removed from the mold.

| | |
|---|---|
| Density (kg/m³) DIN 53,420 | 140 |
| Tensile strength (kp/cm²) DIN 53,571 | 4.3 |
| Elongation at break (%) DIN 53,571 | 50 |
| Resistance of compression at 40% compression (p/cm²) DIN 53,577 | 700 |
| Bond strength between foam foil and ABS foil (p) | 1300 |

EXAMPLE 2

The compound:

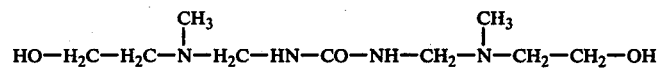

is prepared by reacting 600 parts of urea (10 mol), 2200 parts of aqueous formaldehyde solution (22 mol) and 1500 parts of N-methylethanolamine (20 mol) under the conditions specified in Example 1. 1950 parts of a viscous, water-soluble product which cannot be distilled are obtained.

$C_9H_{22}N_4O_3$ Molecular weight: 234
Analysis of elements:
Calculated: C 46.2%; H 9.4%; O 20.5%; N 23.9%.
Found: — C 44.3%; H 9.0%; O 21.6%; N 24.8%.

3 parts of this compound is reacted with 90 parts of the polyether mentioned in Example 1. 5 parts of triethanolamine, 2 parts of tall oil, 2.5 parts of water and 62 parts of the polyisocyanate mentioned in Example 1 are reacted under the conditions mentioned in Example 1. The resulting foam, compressed to a degree of 1:2, has the following properties:

| | |
|---|---|
| Density (kg/m³) DIN 53,420 | 140 |
| Tensile strength (kp/cm²) DIN 53,571 | 4.9 |
| Elongation at break (%) DIN 53,571 | 55 |
| Resistance to compression at 40% compression (p/cm²) DIN 53,577 | 900 |
| Bond strength between foam and ABS/PVC foil (p) | 2100 |

EXAMPLE 3

90 parts of the polyether mentioned in Example 1, 10 parts of the compound:

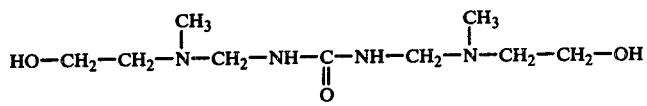

2.5 parts of water and 0.5 parts of N-methyl-N(N'-β-dimethylamino-ethyl)-piperazine and 61 parts of the polyisocyanate mentioned in Example 1 are reacted under the conditions mentioned in Example 1. The resulting foam which has a degree of compression of about 1:3 has the following properties:

| | |
|---|---|
| Density (kg/m³) DIN 53,420 | 150 |
| Tensile strength (kp/cm²) DIN 53,571 | 5.9 |
| Elongation at break (%) DIN 53,571 | 50 |
| Resistance to compression at 40% compression (p/cm²) DIN 53,577 | 1250 |
| Bond strength between foam and ABS/PVC foil (p) | 1300 |

EXAMPLE 4

The compound:

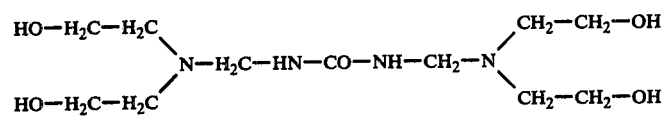

is prepared by reacting 600 parts of urea (10 mol), 2200 parts of aqueous formaldehyde solution (30%, 22 mol) and 2100 parts of diethanolamine (20 mol) under the conditions specified in Example 1. 2830 parts of a viscous, water-soluble, oil which cannot be distilled are obtained.

$C_{11}H_{26}N_4O_5$ Molecular weight: 294
Analysis of elements:
Calculated: C 44.8%; H 8.85%; O 19.1%; N 27.2%.
Found: — C 44.6%; H 9.5%; O 18.4%; N 28.1%.

3 parts of this compound is reacted with 90 parts of the polyester mentioned in Example 1, 5 parts of triethanolamine, 2 parts of tall oil, 2.5 parts of water and 67 parts of polyisocyanate mentioned in Example 1 are reacted under the conditions mentioned in Example 1. The resulting foam which is compressed to a ratio of about 1:2 has the following properties:

| | |
|---|---|
| Density (kg/m³) DIN 53,420 | 140 |
| Tensile strength (kp/cm²) DIN 53,571 | 4.1 |
| Elongation at break (%) DIN 53,571 | 45 |
| Resistance to compression at 40% compression (p/cm²) DIN 53,577 | 900 |
| Bond strength between foam and ABS/PVC foil (p) | 1800 |

EXAMPLE 5

90 parts of the polyether mentioned in Example 1, 10 parts of the compound of the formula:

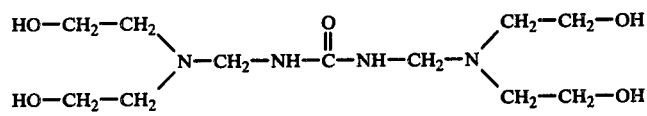

2.5 parts of water, 0.5 parts of N-methyl-N(N'-β-dimethyl-aminoethyl)-piperazine and 68 parts of the polyisocyanate mentioned in Example 1 are reacted under the conditions mentioned in Example 1. The resulting foam has a degree of compression of about 1:2 and the following properties:

| | |
|---|---|
| Density (kg/m³) DIN 53,420 | 150 |
| Tensile strength (kp/cm²) DIN 53,571 | 4.8 |
| Elongation at break (%) DIN 53,571 | 35 |
| Resistance to compression at 40% compression (p/cm²) DIN 53,577 | 1570 |
| Bond strength between foam and ABS/PVC foil (p) | 1250 |

EXAMPLE 6

The compound:

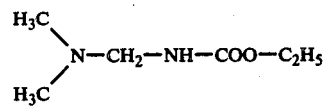

is prepared by introducing 1500 parts of dimethylamine solution (45%, 15 mol) with stirring and water cooling at a reaction temperature of 30° to 45° C. into a suspension of 890 parts of ethyl carbamate (10 mol) in 1200 parts of aqueous formaldehyde solution (30%, 12 mol) which has previously been adjusted to pH 8 to 9 by the addition of dimethylamine solution. The reaction mixture is then stirred for 4 hours at 70° C. and the water is evaporated off under vacuum. The residue distills over at 64° C./0.01 mm (water soluble oil).

Yield: 1.356 kg $C_6H_{14}O_2N_2$ Molecular weight: 146
Analysis of elements:
Calculated: C 49.3%; H 9.6%; O 21.9%; N 19.2%.
Found: C 49.0%; H 9.4%; O 21.8%; N 19.3%.

2 parts of this compound is reacted with 90 parts of the polyester mentioned in Example 1, 5 parts of triethanolamine, 2 parts of tall oil, 2.5 parts of water and 60 parts of the polyisocyanate mentioned in Example 1 are reacted under the conditions mentioned in Example 1. The resulting foam which has a degree of compression of about 1:2 has the following properties:

| | |
|---|---|
| Density (kg/m³) DIN 53,420 | 150 |
| Tensile strength (kp/cm²) DIN 53,571 | 5.2 |
| Elongation at break (%) DIN 53,571 | 45 |
| Resistance to compression at 40% compression (p/cm²) DIN 53,577 | 900 |
| Bond between foam and ABS/PVC foil (p) | 2500 |

EXAMPLE 7

The compound:

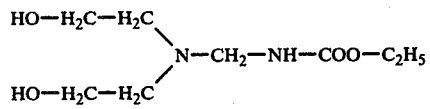

is prepared by reacting 890 parts of ethyl carbamate (10 mol), 1200 parts of aqueous formaldehyde solution (30%, 12 mol) and 1050 parts of diethanolamine (10 mol) together under the conditions described in Example 1. 2.04 kg of a colorless water-soluble oil are obtained.

$C_8H_{18}N_2O_4$ Molecular weight: 206
Analysis of elements:
Calculated: C 46.6%; H 8.75%; O 31.3%; N 13.6%.
Found: C 46.3%; H 9.1%; O 31.4%; N 13.3%.

3 parts of this compound is reacted with 90 parts of the polyether mentioned in Example 1, 5 parts of triethanolamine, 2.5 parts of water, 2 parts of tall oil and 65 parts of the polyisocyanate mentioned in Example 1 under the conditions mentioned in Example 1. The resulting foam which has a degree of compression of about 1:2 has the following properties:

| | |
|---|---|
| Density (kg/m³) DIN 53,420 | 145 |
| Tensile strength (kp/cm²) DIN 53,571 | 5.3 |
| Elongation at break (%) DIN 53,571 | 50 |
| Resistance to compression at 40% compression (p/cm²) DIN 53,577 | 980 |
| Bond strength between foam and ABS/PVC foil (p) | 2600 |

EXAMPLE 8

90 parts of the polyether mentioned in Example 1, 10 parts of the compound

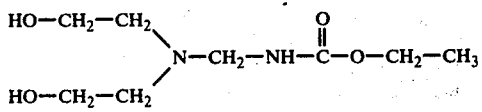

2.5 parts of water, 0.5 parts of N-methyl-N(N'-β-dimethylaminoethyl)-piperazine and 63 parts of the polyisocyanate mentioned in Example 1 are reacted under the conditions mentioned in Example 1.

The resulting foam has a degree of compression of about 1:3 and the following properties:

| | |
|---|---|
| Density (kg/m³) DIN 53,420 | 155 |
| Tensile strength (kp/cm²) DIN 53,571 | 4.4 |
| Elongation at break (%) DIN 53,571 | 40 |
| Compression strength at 40% compression (p/cm²) DIN 53,577 | 1420 |
| Bond strength between foam and ABS/PVC foil (p) | 1760. |

EXAMPLE 9

Preparation of:

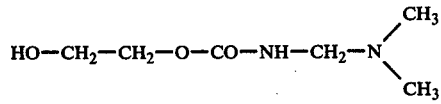

N-dimethyl amino methylene-N'-β-hydroxy ethyl urethane.

About 300 parts by volume of 30% aqueous formaldehyde solution (3 mols) are added with stirring to about 315 parts of β-hydroxy ethyl urethane (3 mols), followed by the dropwise addition while cooling with ice water of about 360 parts by volume of a 52% aqueous dimethyl amine solution (3.5 mols) at a temperature of up to about 40° C. After stirring for about 1 hour at about 40° C., the mixture is heated for about 2 hours to between 70° C. to 80° C. and then concentrated by evaporation in vacuo. A water soluble oil which crystallizes after prolonged standing and has a melting point of 60° C. to 61° C. after repeated recrystallization from ethyl acetate.

Yield: 440 parts $C_6H_{14}N_2O_3$ Molecular weight: 162
Analysis of elements:
Calculated: C 44.4%; H 8.64%; O 29.6%; N 17.29%;
Found: C 43.7%; H 8.5%; O 30.5%; N 16.6%;

About 10 parts of this compound, about 90 parts of a polyether having a molecular weight of about 4800, obtained by the chemical addition of propylene oxide (87% by weight) and ethylene oxide (13% by weight) to trimethylol propane, about 5 parts of tall oil and about 2.5 parts of water are mixed together. This mixture is mixed with thorough stirring with about 60 parts of a polyphenyl-polymethylene-polyisocyanate which is obtained by phosgenating an aniline-formaldehyde condensate and which has an NCO-content of about 31%. The foamable reaction mixture is introduced into an aluminum mold lined with a vacuum-formed ABS/PVC film (film of an acrylonitrile-butadiene-styrene copolymer containing polyvinyl chloride as plasticizer). The foaming reaction begins immediately after introduction of the reaction mixture. The compression ratio is about 1:2. A foam with the following properties is obtained after demolding:

| | | |
|---|---|---|
| Density DIN 53,420 | (kg/m³) | 160 |
| Tensile strength DIN 53,571 | (kp/cm²) | 6.3 |
| Breaking elongation DIN 53,571 | (%) | 65 |
| Hardness at 40% compression DIN 53,577 | (p/cm²) | 1100 |
| Bond strength between | | |

EXAMPLE 10

About 90 parts of the polyether used in Example 9, about 15 parts of the compound

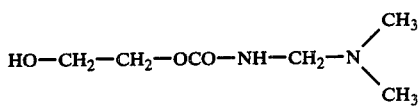

prepared in accordance with Example 9, about 2.5 parts of water and about 57 parts of the polyisocyanate used in Example 9 are reacted under the conditions of Example 9.

The foam obtained has the following properties for a compression ratio of about 1:2:

| | | |
|---|---|---|
| Density DIN 53,420 | (kg/m$^3$) | 160 |
| Tensile strength DIN 53,571 | (kp/cm$^2$) | 5.8 |
| Breaking elongation DIN 53,571 | (%) | 70 |
| Hardness at 40% compression DIN 53,577 | (p/cm$^2$) | 1150 |
| Bond strength between foam and ABS/PVC film | (p) | 1100–1230. |

EXAMPLE 11

Preparation of

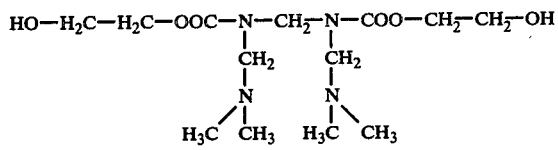

About 210 parts of β-hydroxyalkylurethane (2 mols) are dissolved in about 1000 parts of water and after addition of about 100 parts of a 30 percent aqueous formaldehyde solution (1 mol) and about 3 parts of concentrated hydrochloric acid, the reaction mixture was stirred at room temperature for about 3 days. Then water was distilled off at 60° to 70° C./12 mm Hg. 222 parts of a viscous oil were obtained.

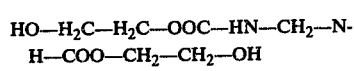

$C_7H_{14}N_2O_6$ Molecular weight: 222.
Analysis of elements:
Calculated: C 37.8; H 6.3; N 12.6; O 43.3%. Found: C 37.6; H 6.5; N 12.2; O 44.1%.

About 220 parts of an aqueous dimethylamine solution (45 percent by weight) (2.2 mols) and 220 parts of a 30 percent aqueous formaldehyde solution (2.2 mols) are added to 222 parts of the above-mentioned reaction product. The temperature increases to 60° to 70° C. After that the mixture is heated at 70° C. for 3 hours, followed by removal of the water in vacuo. 272 parts of an oil is obtained, which cannot be purified by distillation.

$C_{13}H_{28}N_4O_6$ Molecular weight: 336.
Analysis of elements:
Calculated: C 46.5%; H 8.3%; N 16.6%; O 28.5%.
Found: C 42.3%; H 7.8%; N 13.5%; O 35.2%.

About 15 parts of this compound, about 90 parts of the polyether used in Example 9, about 5 parts of tall oil, about 2.5 parts of water and about 57 parts of the polyisocyanate used in Example 9 are reacted under the conditions of Example 9.

The foam obtained has the following properties for a compression ratio of about 1:2:

| | | |
|---|---|---|
| Density DIN 53,420 | (kg/m$^3$) | 135 |
| Tensile strength DIN 53,571 | (kp/cm$^2$) | 3.1 |
| Breaking elongation DIN 53,571 | (%) | 45 |
| Hardness at 40% compression DIN 53,577 | (p/cm$^2$) | 850 |
| Bond strength between foam and ABS/PVC film | (p) | 1100–1320. |

EXAMPLE 12

About 90 parts of the polyether used in Example 9, about 15 parts of the compound

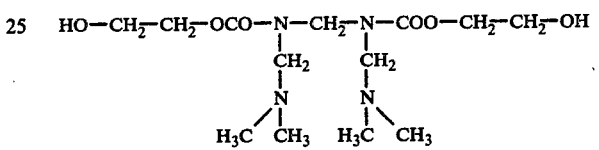

prepared in accordance with Example 11, about 2.5 parts of water, about 0.5 parts of N-methyl-N-(N'-β-dimethyl amino ethyl)-piperazine and about 57 parts of the polyisocyanate used in Example 9 are reacted under the conditions of Example 9.

The foam formed has the following properties for a compression ratio of about 1:2:

| | | |
|---|---|---|
| Density DIN 53,420 | (kg/m$^3$) | 150 |
| Tensile strength DIN 53,571 | (kp/cm$^2$) | 3.1 |
| Breaking elongation DIN 53,571 | (%) | 45 |
| Hardness at 40% compression DIN 53,577 | (p/cm$^2$) | 900 |
| Bond strength between foam and ABS/PVC film | (p) | 1100–1410. |

EXAMPLE 13

Preparation of

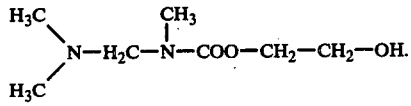

About 110 parts by volume of a 30% aqueous formaldehyde solution (1.1 mol) are introduced into about 119 parts of N-methyl-β-hydroxy ethyl urethane (1 mol), followed by the dropwise addition of about 125 parts by volume of a 52% aqueous dimethyl amine solution (1.2 mols) while cooling with ice and stirring so that the temperature remains below about 40° C. The mixture is then heated for about 1 hour to between 70° C. to 80° C., concentrated by evaporation in vacuo and distilled.
b.p. 105° C./0.07 cc. Hg.
Yield: 155 parts $C_7H_{16}O_3N_2$ Molecular weight: 176
Analysis of elements:

| | | |
|---|---|---|
| foam and ABS/PVC film | (p) | 1150–1280. |

Calculated: C 48.0%; H 9.15%; O 27.4%; N 16.0%.
Found: C 47.8%; H 9.5%; O 27.6%; N 15.8%.

About 15 parts of this compound, about 90 parts of a polyether used in Example 9, about 2.5 parts of water are mixed together. This mixture is thoroughly mixed with about 58 parts of the polyphenyl-polymethylene-polyisocyanate used in Example 9. The foamable reaction mixture is introduced into an aluminum mold lined with a vacuum-formed ABS/PVC film. The foaming reaction begins following introduction of the reaction mixture. The foam obtained has the following properties for a compression ratio of about 1:2.5:

| | | |
|---|---|---|
| Density DIN 53,420 | (kg/m³) | 140 |
| Tensile strength DIN 53,571 | (kp/cm²) | 6.2 |
| Breaking elongation DIN 53,571 | (%) | 70 |
| Hardness at 40% compression DIN 53,577 | (p/cm²) | 694 |
| Bond strength between foam and ABS/PVC film | (p) | 3100–3920 |

EXAMPLE 14

Preparation of

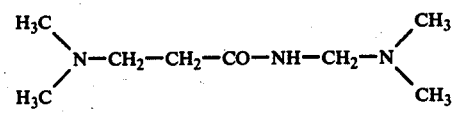

N-dimethyl amino methylene-β-dimethyl amino propionic acid amide.

49,400 parts by volume (42,000 parts) of a 52% aqueous dimethyl amine solution (484 mols) are added, while stirring and cooling with water, into a suspension, contained in a vessel with an internal temperature of between 30° C. to 45° C., of 15,620 parts of acrylamide (220 mols) in 22,000 parts of 30% aqueous formaldehyde solution (220 mols) whose pH-value is adjusted beforehand to between 8 and 9 by the addition of dimethyl amine. The mixture is stirred for about 4 hours at about 70° C. and the water evaporated off in vacuo. The final traces of water are removed at a vacuum of about 3.5 mm Hg, during which the internal temperature of the vessel does not exceed about 60° C.

Yield: 32,900 parts (86.5% of the theoretical) $C_8H_{19}N_3O$

Boiling point at 0.2 mm Hg: 118° C. to 120° C.
Molecular weight: 173
Analysis of elements:
Calculated: C 55.5%; H 11.0%; O 9.25%; N 24.3%.
Found: C 54.9%; H 10.8%; O 10.1%; N 23.2%.

About 0.5 parts of this compound, about 90 parts of the polyether of Example 9, about 5 parts of triethanolamine, about 2.5 parts of water and about 60 parts of the polyisocyanate used in Example 9 are reacted under the conditions of Example 9.

The foam obtained has the following properties for a compression ratio of about 1:2.5:

| | | |
|---|---|---|
| Density DIN 53,420 | (kg/m³) | 165 |
| Tensile strength DIN 53,571 | (kp/cm²) | 5.1 |
| Breaking elongation DIN 53,571 | (%) | 60 |
| Hardness at 40% compression DIN 53,577 | (p/cm²) | 1340 |
| Bond strength between foam and ABS/PVC film | (p) | 1150–1290. |

Comparison Example 1

About 90 parts of the polyether of Example 9, about 5 parts of triethanolamine, about 2 parts of tall oil, about 2.5 parts of water, about 0.5 parts of N-methyl-N-(N'-β-dimethyl amino ethyl)-piperazine and about 60 parts of the polyisocyanate used in Example 9, are reacted under the conditions of Example 9.

The foam obtained has the following properties for a compression ratio of about 1:2:

| | | |
|---|---|---|
| Density DIN 53,420 | (kg/m³) | 150 |
| Tensile strength DIN 53,571 | (kp/cm²) | 3.0 |
| Breaking elongation DIN 53,571 | (%) | 35 |
| Hardness at 40% Compression | (p/cm²) | 950 |
| Bond strength between foam and ABS/PVC film | (p) | 300–800 |

Comparison Example 2

About 90 parts of the polyether of Example 9, about 10 parts of the compound

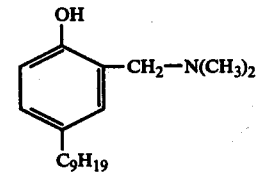

about 2.5 parts of water and about 52 parts of the polyisocyanate used in Example 9, are reacted under the conditions of Example 9.

The foams obtained under went such extensive shrinking that it was not possible to measure their mechanical properties.

Comparison Example 3

90 parts of the polyether mentioned in Example 1, 5 parts of triethanolamine, 2 parts of tall oil, 2.5 parts of water, 0.5 parts of N-methyl-N(N'-β-dimethylaminoethyl)-piperazine and 60 parts of the polyisocyanate mentioned in Example 1 are reacted under the conditions mentioned in Example 1.

The resulting foam has a compression ratio of about 1:2 and the following properties:

| | | |
|---|---|---|
| Density DIN 53,420 | (kg/m³) | 150 |
| Tensile strength DIN 53,571 | (kp/cm²) | 3.0 |
| Elongation at break DIN 53,571 | (%) | 35 |
| Resistance to compression at 40% compression DIN 53,577 | (p/cm²) | 950 |
| Bond strength between foam and ABS/PVC foil | (p) | 300–800 |

The following are further examples of the preparation of Mannich bases which may be employed in the practice of the present invention.

EXAMPLE 15

Preparation of:

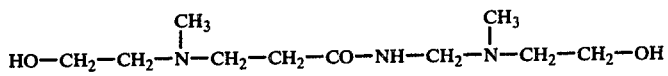

N-methyl-N-β-hydroxy ethyl amino-β-propionamido-N'-methylene-N"-methyl-N"-β-hydroxy ethyl amine.

About 71 parts of acrylamide (1 mol), about 110 parts by volume of a 30% aqueous formaldehyde solution (1.1 mol) and about 150 parts of N-methyl ethanolamine (2 mols) are combined while stirring, the temperature increasing spontaneously to about 50° to 60° C. The mixture is then heated for about 2 hours to about 70° to 80° C. and the water distilled off in vacuo, leaving behind a viscous water-soluble oil.

Yields: 230 parts $C_{10}H_{23}O_3N_3$; Molecular weight = 233.

Analysis of elements:
Calculated: C 51.5%; H 9.9%; O 20.6%; N 18.0%.
Found: C 50.8%; H 9.8%; O 21.6%; N 17.7%.

EXAMPLE 16

Preparation of

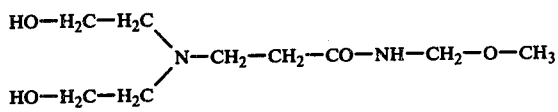

N-di-β-hydroxy ethyl amino-β-propionamido-N'-methylene methyl ether.

About 115 parts of acrylamido-N-methylol methyl ether (for preparation see "Die Makromolekulare Chemie," Vol. 57, page 45 (1962)) (1 mole) are added dropwise with stirring between about 40° C. to 70° C. to about 105 parts of di-β-hydroxy ethyl amine. The mixture is stirred for about 6 hours between 80° C. to 90° C. and after cooling a water-soluble viscous oil is obtained.

Yield: 220 parts $C_9H_{20}N_2O_4$; Molecular weight: 220
Analysis of elements:
Calculated: C 49.1%; H 9.1%; N 12.7%; O 29.1%.
Found: C 48.2%; H 9.2%; N 13.0%; O 29.1%.

EXAMPLE 17

Preparation of:

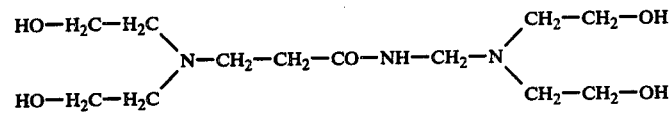

N-di-β-hydroxy ethyl amino-β-propionamido-N'-methylene-N"-di-β-hydroxy ethyl amine.

About 71 parts of acrylamide (1 mol) are introduced while stirring into about 100 parts by volume of a 30% aqueous formaldehyde solution (1 mol), followed by the dropwise addition with cooling of about 210 parts of diethanolamine at a temperature below about 40° C. The mixture is then heated for about 3 hours to about 70° to 80° C. and the water distilled off in vacuo. A highly viscous, water-soluble oil is obtained.

Yield: 275 parts $C_{12}H_{27}N_3O_5$; Molecular weight: 293
Analysis of elements:
Calculated: C 49.2%; H 9.2%; N 14.3%; O 27.3%.
Found: C 49.6%; H 9.8%; N 13.8%; O 27.9%.

EXAMPLE 18

The compound:

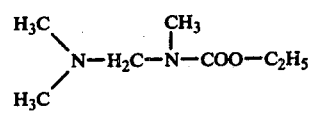

is prepared by introducing 1500 parts of dimethyl amine solution (45%, 15 mol) with stirring and water cooling at a reaction temperature of 30° to 45° C. into a suspension of 1030 parts of N-methylethylurethane (10 mol) in 1200 parts of aqueous formaldehyde solution (30%, 12 mol) which has been adjusted to pH 8 to 9 by the addition of dimethyl amine solution. The reaction is then stirred for 4 hours at 70° C. and the water is evaporated off under vacuum. 1270 parts of a product which distills over at 43° C./0.5mm are obtained (water soluble oil).

Yields: $C_7H_{16}O_2N_2$; Molecular weight: 160
Analysis of elements:
Calculated: C 52.5%; H 10.0%; O 20.0%; N 17.5%.
Found: C 52.2%; H 9.8%; O 20.2%; N 17.3%.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. Semi-rigid polyurethane foams having high bond strengths with acrylonitrile-butadiene-styrene or polyvinyl chloride polymers prepared by a process comprising reacting in the presence of blowing agents and optionally in the presence of catalysts and/or stabilizers, organic polyisocyanates with polyhydroxyl compounds having a molecular weight of about 800 to about 10,000 in the presence of from 3 to 50 parts by weight per 100 parts by weight of polyhydroxyl compound, of a Mannich base of the formula:

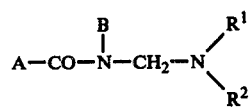

wherein
A is (1) or $-OR^9$,

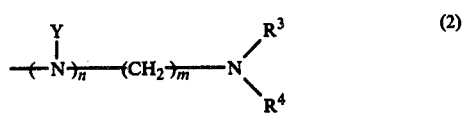

(2)

-continued

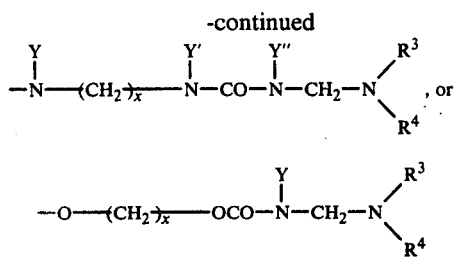

m is an integer of from 1 to 8, preferably 1 or 2;
n is an integer equal to 1 when m is 1 and otherwise is 0.
x is an integer of from 1 to 6;
B is —H, $C_1$–$C_{16}$ alkyl, or when A is (1) or A is (2) and n is 0,

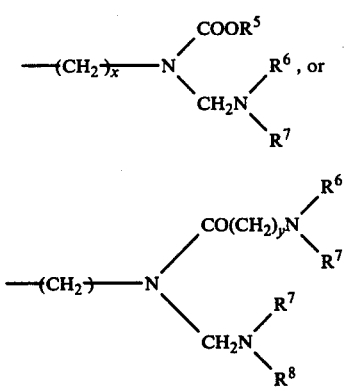

but preferably —H;
y is an integer from 2 to 8, but preferably 2;
$R^1$ through $R^9$ are the same or different and are $C_1$–$C_{12}$ alkyl and,
Y, Y′ and Y″ are the same or different and are —H or $C_1$–$C_{16}$ alkyl, the amounts of reactants being such that the NCO to active hydrogen ratio is from about 0.9:1 to about 1.1:1.

2. In a process for producing semi-rigid polyurethanes by the reaction of (1) organic polyisocyanates, (2) compounds containing at least two reactive hydrogen atoms and having a molecular weight of 400 to 10,000, and (3) compounds having a cross-linking or chain-lengthening action, optionally in the presence of activators, blowing agents, and/or stabilizers, the improvement which comprises including in the reaction mixture from 3 to 50 parts by weight, based on 100 parts by weight of the active hydrogen containing material of a Mannich base of the formula:

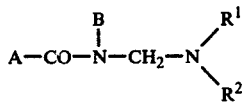

wherein
A is (1) - $OR^9$,

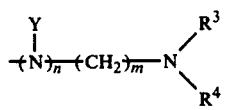

-continued

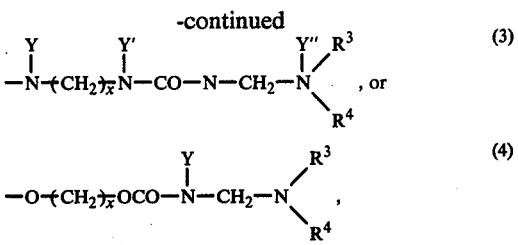

m is an integer of from 1 to 8, preferably 1 or 2;
n is an integer equal to 1 when m is 1 and otherwise is 0;
x is an integer of from 1 to 6;
B is —H, $C_1$–$C_{16}$ alkyl, or when A is (1) or A is (2) and n is 0,

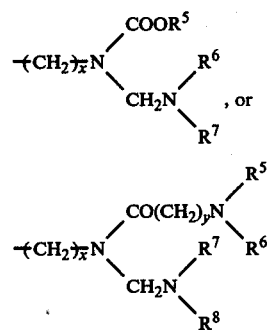

but preferably —H;
y is an integer from 2 to 8, but preferably 2;
$R^1$ through $R^9$ are the same or different and are $C_1$–$C_{12}$ alkyl; and
Y, Y′ and Y″ are the same or different and are —H or $C_1$–$C_{16}$ alkyl.

3. The polyurethane of claim 1 wherein the Mannich base has the formula

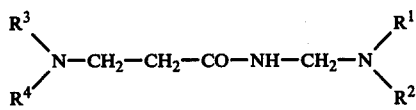

and $R^1$, $R^2$, $R^3$ and $R^4$ are as defined in claim 1.

4. The polyurethane of claim 3 wherein the Mannich base has the formula

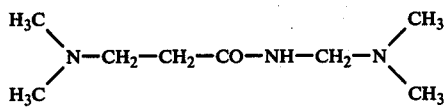

5. In the process of claim 2 the further improvement wherein the Mannich base has the formula

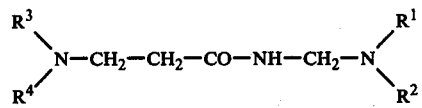

and $R^1$, $R^2$, $R^3$ and $R^4$ are as defined in claim 2.

6. In the process of claim 5 the further improvement wherein the Mannich base has the formula

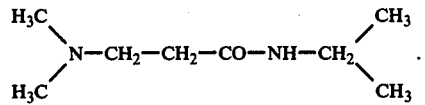

* * * * *